(12) United States Patent  (10) Patent No.: US 10,788,684 B2
Fayolle  (45) Date of Patent: Sep. 29, 2020

(54) METHOD FOR ADAPTING THE OPTICAL FUNCTION OF AN ADAPTIVE OPHTHALMIC LENSES SYSTEM

(71) Applicant: Essilor International, Charenton-le-Pont (FR)

(72) Inventor: Romain Fayolle, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 14/425,173

(22) PCT Filed: Sep. 5, 2013

(86) PCT No.: PCT/EP2013/068377
§ 371 (c)(1),
(2) Date: Mar. 2, 2015

(87) PCT Pub. No.: WO2014/037447
PCT Pub. Date: Mar. 13, 2014

(65) Prior Publication Data
US 2015/0248020 A1  Sep. 3, 2015

(30) Foreign Application Priority Data
Sep. 6, 2012 (EP) .................................. 12306067

(51) Int. Cl.
*G02C 7/08* (2006.01)
*G02C 7/10* (2006.01)
*A61B 3/113* (2006.01)
(52) U.S. Cl.
CPC .............. *G02C 7/083* (2013.01); *A61B 3/113* (2013.01); *G02C 7/101* (2013.01)
(58) Field of Classification Search
CPC ................................. G02C 7/083; G02C 7/101
(Continued)

(56) References Cited

U.S. PATENT DOCUMENTS 5,841,507 A    11/1998  Barnes
6,244,703 B1 *  6/2001  Resnikoff .............. G02C 7/101
                                                     351/44

(Continued)

FOREIGN PATENT DOCUMENTS

DE         19714434      10/1998
DE      102004062277      7/2006
(Continued)

OTHER PUBLICATIONS

International Preliminary Report on Patentability and Written Opinion of the International Searching Authority, dated Mar. 10, 2015, for International Application No. PCT/EP2013/068377 (6 pages).

(Continued)

*Primary Examiner* — Travis S Fissel
(74) *Attorney, Agent, or Firm* — Oblon, McClelland, Maier & Neustadt, L.L.P.

(57) ABSTRACT

Methods for adapting the optical function of an adaptive ophthalmic lenses system are provided. Said methods comprise an adaptive ophthalmic lenses system providing step during which an adaptive ophthalmic lenses system is provided. An acquisition step during which the scene in front of the wearer is acquired may be provided. A gazing zone determining step during which a gazing zone is determined may be included, the gazing zone being a zone of images of the scene acquired comprising the gazing direction of the wearer. A parameter determining step during which the value of at least one parameter of the images of the scene is determined may be provided. An adaptation step may be included during which the optical function of active ophthalmic lenses are adapted according to the value of the at least one parameter determined during the parameter determining step.

20 Claims, 1 Drawing Sheet

(58) Field of Classification Search
USPC ........ 351/159.39, 159.4, 49, 159.65, 159.59,
351/159.6, 159.01, 159.09
See application file for complete search history.

(56) References Cited

U.S. PATENT DOCUMENTS

| | | | | |
|---|---|---|---|---|
| 6,456,262 | B1* | 9/2002 | Bell | A61B 3/113 345/472 |
| 8,042,947 | B1* | 10/2011 | Eberl | A61B 3/113 351/246 |
| 2002/0085843 | A1* | 7/2002 | Mann | E03C 1/057 396/374 |
| 2003/0151674 | A1* | 8/2003 | Lin | G06K 9/036 348/222.1 |
| 2005/0175218 | A1* | 8/2005 | Vertegaal | A61B 3/113 382/103 |
| 2008/0170203 | A1* | 7/2008 | Esser | G02C 7/085 351/159.75 |
| 2009/0195749 | A1* | 8/2009 | Blum | G02B 27/017 351/159.44 |
| 2010/0053555 | A1* | 3/2010 | Enriquez | A61B 3/113 351/210 |
| 2011/0051008 | A1* | 3/2011 | Lee | G06T 5/009 348/678 |
| 2011/0249910 | A1* | 10/2011 | Henderson | G06K 9/00134 382/278 |
| 2012/0075168 | A1* | 3/2012 | Osterhout | G02B 27/017 345/8 |
| 2012/0236257 | A1* | 9/2012 | Hillis | G02C 7/04 351/205 |

FOREIGN PATENT DOCUMENTS

| | | |
|---|---|---|
| JP | 2008-537608 A | 9/2008 |
| JP | 2008282031 | 11/2008 |
| JP | 2009-93201 A | 4/2009 |
| JP | 2009-294654 A | 12/2009 |
| JP | 2011125051 | 1/2011 |
| WO | WO 03077012 | 9/2003 |
| WO | WO 2006060683 | 6/2006 |
| WO | 2011163080 | 12/2011 |
| WO | WO 2011153112 | 12/2011 |

OTHER PUBLICATIONS

International Search Report dated Nov. 4, 2013, for International Application No. PCT/EP2013/068377 (4 pages).
Extended European Search Report and European Search Opinion, dated Mar. 4, 2013, for European Application No. 12306067.5 (6 pages).
Japanese Office Action dated Jul. 23, 2019, in Patent Application No. 2015-530389, 18 pages (with English translation).

* cited by examiner

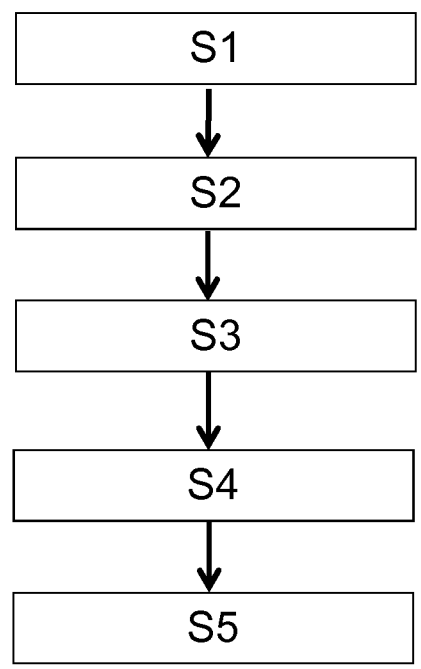

METHOD FOR ADAPTING THE OPTICAL FUNCTION OF AN ADAPTIVE OPHTHALMIC LENSES SYSTEM

CROSS REFERENCE TO RELATED APPLICATIONS

This application is a U.S. national stage application of International Application No. PCT/EP2013/068377 filed Sep. 5, 2013, which claims the benefit of priority to EP Application No. 12306067.5, filed Sep. 6, 2012; the entirety of each of said applications is incorporated herein by reference.

FIELD OF THE INVENTION

The invention relates to a method for adapting the optical function of an adaptive ophthalmic lenses system.

BACKGROUND

The discussion of the background of the invention herein is included to explain the context of the invention. This is not to be taken as an admission that any of the material referred to was published, known or part of the common general knowledge at the priority date of any of the claims.

Numerous attempts have been made to adapt certain optical features of ophthalmic lenses, or spectacles eyeglasses, dynamically in order to improve comfort or in order to provide new functions for wearers of the lenses.

For example, the light transmission of lenses can be reduced under conditions of high brightness, and can be increased again when ambient light returns to a normal or low level of intensity.

Photochromic lenses perform this function, but the variations in light transmission provided by such lenses are determined by the intensity of ultraviolet radiation illuminating the lenses. The light transmission level adopted by photochromic lenses is therefore unsuitable under certain circumstances. In particular, photochromic lenses inside a car remain in a state of high transparency whatever the level of sunlight. A car driver is therefore not protected against being dazzled when wearing spectacles with photochromic lenses.

Electro-optical systems enable optical features of optical lenses to be controlled by means of an electrical stimulus.

By way of example, the light transmission of an electrochromic lens or the local dioptric power can vary in response to an electric current. Modifying local dioptric power enables there to be adaptation of the ophthalmic correction of the lenses, for example according to the activity of the wearer, reading, driving, playing sport etc.

It appears very advantageous to make such variation automatic switching. In this case a sensor is required.

One object of the invention is to provide a method for adapting the optical function of an adaptive ophthalmic lenses system according to information providing from the scene the wearer is looking at.

SUMMARY

To this end, the invention proposes a method for adapting the optical function of an adaptive ophthalmic lenses system, the method comprising:

an adaptive ophthalmic lenses system providing step during which an adaptive ophthalmic lenses system is provided, the adaptive ophthalmic lenses system comprising:

a pair of adaptive ophthalmic lenses, and at least one light sensor configured to acquire the scene facing the wearer through a functionalized optical system providing functionalized images of the scene, an acquisition step during which the scene in front of the wearer is acquired by the light sensor through the functionalized optical system, a gazing zone determining step during which a gazing zone is determined, the gazing zone being a zone of the images of the scene acquired during the acquisition step comprising the gazing direction of the wearer, a parameter determining step during which the value of at least one parameter of the images of the scene acquired during the acquisition step is determined in the gazing zone of the images of the scene, an adaptation step during which the optical function of the active ophthalmic lenses system is adapted according to the value of the at least one parameter determined during the parameter determining step.

Advantageously, the method according to the invention can be used to adapt the optical function of an adaptive ophthalmic lenses system according to parameters of the scene being observed by the wearer.

For example, when the wearer drives a car, the optical function of the adaptive ophthalmic lenses can be adapted to the fact that the wearer passes an opposite car with beam headlamps turned on and adapted again once the opposite car has passed.

The method according to the invention can be used when a student is required to look alternatively at near distance to write and a far distance to read a board. The invention may also be used by a user looking alternatively at his smartphone and at a presentation or another person at a meeting. Using the method of the invention, the optical function of the adaptive ophthalmic lenses can easily be adapted to what, in particular at what distance, the wearer is looking at.

According to further embodiments which can be considered alone or in combination:

the adaptive ophthalmic lenses system provided during the adaptive ophthalmic lenses system providing step comprises an eye tracking device arranged to determine the gazing direction of the wearer, and the method further comprises a calibration step, during which the eye tracking device is calibrated according to geometrical and eye-related features of the wearer, and/or the functionalized optical system is arranged so as to have at least one working distance, and during the parameter determining step, at least one parameter is related to the sharpness of the functionalized images of the scene in the gazing direction, and/or the functionalized optical system is arranged so as to have at least two working distances, during the acquisition step the scene in front of the wearer is acquired by the light sensor through the functionalized optical system using the at least two working distances, the method further comprises after the parameter determining step a comparison step during which the values of the sharpness in the gazing zone of the functionalized images of the scene obtained through the functionalized optical system with the different working distances are compared, and during the adaptive step the active ophthalmic lenses are adapted so as to provide clear vision to the wearer at the working distance corresponding to the working distance of the functionalized optical system used to obtain the functionalized images having the greatest sharpness value, and/or the method further comprises after the parameter determining step a comparison step during which the sharpness of the functionalized images of the scene in the gazing direction is compared to a threshold value and during the adaptive step the active ophthalmic lenses is adapted so as to provide clear vision to the wearer at the working distance when the sharpness is greater or equal to the threshold value, and/or one of the at least one working distances is smaller than or equal to 60 centimeters (cm), and/or one of the at least one working distances is greater than or equal to 2 meters (m), and/or during the parameter determining step, the luminosity in the gazing direction is determined and the active ophthalmic lenses system is configured so as to adapt to the determined luminosity, and/or the light sensor is a linear or matricial array of light sensors, for example a camera, and/or the parameter determining step is completed by a prior feature recognition step, during which objects in gaze direction are analyzed, in order to establish whether the wearer needs a complement of acuity, which is advantageous, for example when human faces, written characters, computer or mobile device screens, road signs, do occur in the gazing direction.

According to a further aspect, the invention relates to a computer program product comprising one or more stored sequences of instructions that are accessible to a processor and which, when executed by the processor, causes the processor to carry out the acquisition, parameter determining and adaptive steps of the methods described.

The invention further relates to a computer readable medium carrying one or more sequences of instructions of the computer program product described.

Furthermore, the invention relates to a program which makes a computer execute the methods described.

The invention also relates to a computer-readable storage medium having a program recorded thereon; where the program makes the computer execute the methods described.

The invention further relates to a device comprising a processor adapted to store one or more sequence of instructions and to carry out at least one of the steps of the methods described.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or a Field Programmable Gate Array ("FPGA") or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs described herein in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Other features and advantages of the present invention will become apparent from the following description of non-limitative embodiments, with reference to the attached drawing in which:

FIG. 1 is a flowchart of the different steps of a method as described herein.

DESCRIPTION

According to an embodiment illustrated on FIG. 1, the method for adapting the optical function of an adaptive ophthalmic lenses system comprises:

an adaptive ophthalmic lenses system providing step S1,
an acquisition step S2,
a gazing zone determining step S3,
a parameter determining step S4,
an adaptation step S5.

During the adaptive ophthalmic lenses system providing step S1, an adaptive ophthalmic lenses system is provided.

The adaptive ophthalmic lenses system may comprise a pair of adaptive ophthalmic lenses, and at least one light sensor, for example a camera, configured to acquire the scene facing the wearer through a functionalized optical system providing functionalized images of the scene.

The pair of adaptive ophthalmic lenses system may be of the kind known from the skilled person. Examples of adaptive ophthalmic lenses systems are disclosed in FR 2910642 or FR 2871586.

According to an embodiment, the pair of adaptive ophthalmic lenses described herein comprise two electro-optical lenses mounted on a spectacle frame.

The light sensor of the adaptive ophthalmic lenses system is advantageously a small type of light sensor, for example a smart phone type of camera, so as to be as discrete as possible. For example the light sensor, may be mounted on the frame holding the pair of adaptive ophthalmic lenses so as to acquire the scene in front of the wearer.

Advantageously, the light sensor is a camera having a large angle of view allowing acquiring a large part of the scene facing the wearer, consistent with the wearer's field of view through eyeglasses, when rotating eyeballs.

The light sensor is provided with a functionalized optical system so as to provide functionalized images of the scene in front of the wearer.

During the acquisition step S2, the scene in front of the wearer is acquired by the light sensor through the functionalized optical system.

The functionalized optical system may be arranged so as to simulate an ametropia, for example the wearer's ametropia.

A gazing zone is determined during the gazing zone determining step. The gazing zone corresponds to the zone of the images of the scene acquired during the acquisition step comprising the gazing direction of the wearer.

According to an embodiment described herein, the gazing zone may be determined by using an eye tracking device.

For example, the adaptive ophthalmic lenses system may comprise an eye tracking device arranged to determine the gazing direction of the wearer. The eye tracking device may be mounted on the frame holding the pair of adaptive ophthalmic lenses.

So as to determine accurately the gazing zone, the method described herein may further comprise prior to the acquisition step S2 a calibration step.

During the calibration step, the eye tracking device may be calibrated according to geometrical and/or eye-related features of the wearer. Inter-pupillary distance, nose and ear shape and height are examples of geometrical parameters that may be considered as geometrical feature. Iris size and color are examples of eye-related features that may be considered during the calibration step.

According to an embodiment described herein, the gazing direction may be determined using a single imager to perform the functions of eye-tracking and observation of the scene. In this case, a switchable mirror system (tilting, or digital micromirror device (DMD)) and an optical system allowing to image properly in different configurations could be used.

The value of at least one parameter of the images of the scene acquired during the acquisition step is determined during the parameter determining step S4.

According to an embodiment described herein, the value of at least one parameter of the images of the scene is determined in the gazing zone.

Among the parameters of the images of the scene that can be determined, one may determine the sharpness of and/or the luminosity the images of the scene, in particular in the gazing zone.

During the adaptation step S5, the optical function of the active ophthalmic lenses system is adapted according to the value of the parameters determined during the parameter determining step. The adaptation of the optical function may be limited to the zone of the optical lenses through which the wearer looks when looking at the gazing zone, so as to reduce the processing time.

For example, the value of the parameter can provide information concerning the distance of the object of the scene situated in the gazing zone. The optical function can thus be adapted to the gazing distance.

The value of the parameters determined during the determining step may also provide information on the luminosity in the gazing zone. For example, when the wearer is driving and passes an opposite car with beam headlamps turned on, the parameter may provide information on an increase in luminosity in the gazing zone and during the adaptation zone the light transmission of the lenses of the adaptive ophthalmic lenses system can be adjusted so as to prevent the wearer from being dazzled.

According to an embodiment described herein, the functionalized optical system through which the light sensor, for example the camera, acquires the scene facing the wearer is arranged so as to have a working distance.

For example, the functionalized optical system may be an optical lens adapted to as to provide clear images of object at a given range.

The optical system may be adapted so as to be consistent with myopia or presbyopia of the wearer.

During the parameter determining step, the sharpness of the image or object detected in the gazing zone can be determined.

The method may further comprise after the parameter determining step a comparison step during which the sharpness or sharpness variation of the functionalized images of the scene or objects detected in the gazing direction is compared to a threshold value.

During the adaptive step, the active ophthalmic lenses is adapted so as to provide clear vision to the wearer at the working distance when the sharpness or sharpness variation is greater or equal to the threshold value.

For example, for a wearer having myopia, the functionalized optical system is adapted to provide a clear image of object at far distance, for example at distances greater than 2 meters. During the parameter determining step the sharpness of the image or object detected in the gazing zone is determined and compared to a threshold value during the comparison step.

When the scene in the gazing zone is at a distance greater than or equal to the working distance of the functionalized optical system, the value of the parameter is greater than the threshold value. Thus, the optical function of the active ophthalmic lenses system is adapted so as to provide optical correction to the wearer looking at a part of the scene that is at far distance and requires optical correction.

Whereas, when the scene in the gazing zone is at a distance smaller than or equal to the working distance of the functionalized optical system, the value of the parameter is smaller than the threshold value. Thus, the optical function of the active ophthalmic lenses system is adapted so as to provide no correction to the wearer looking at a part of the scene that is at near distance and does not require optical correction.

For example, for a wearer having hyperopia, the functionalized optical system is adapted to provide a clear image of object at near distance, for example, at distances smaller than or equal to 60 centimeters. During the parameter determining step, the sharpness of the image or object detected in the gazing zone is determined and compared to a threshold value during the comparison step.

When the scene in the gazing zone is at a distance smaller than or equal to the working distance of the functionalized optical system, the value of the parameter is greater than the threshold value. Thus, the optical function of the active ophthalmic lenses system is adapted so as to provide optical correction to the wearer looking at a part of the scene that is at near distance and requires optical correction.

Whereas, when the scene in the gazing zone is at a distance greater than or equal to the working distance of the functionalized optical system, the value of the parameter is smaller than the threshold value. Thus, the optical function of the active ophthalmic lenses system is adapted so as to provide no correction to the wearer looking at a part of the scene that is at far distance and does not require optical correction.

According to an embodiment described herein, the functionalized optical system is arranged to have at least two working distances. For example the functionalized optical system may be a bi-focal or a progressive addition lens having different distance vision zone. The functionalized optical system may also be an active optical lens of which the focal distance may be adapted.

According to such embodiment described herein, the method further comprises after the parameter determining step a comparison step during which the values of the sharpness in the gazing zone of the functionalized images of the scene obtained through the functionalized optical system with the different working distances are compared.

During the adaptive step the active ophthalmic lenses are adapted so as to provide clear vision to the wearer at the working distance corresponding to the working distance of the functionalized optical system used to obtain the functionalized images having the greatest sharpness value.

Such embodiment may be particularly adapted for wearers requiring different optical correction at different viewing distance or to provide improved detection robustness and accuracy. For example such embodiment may be particularly advantageous for wearers having presbyopia.

The method described herein may comprise prior to the parameter determining step a feature recognition step.

Objects in the gaze zone are analyzed during the feature recognition step. The parameter determining step can also be performed via a calculation limited to the zones of the image corresponding to detected pertinent objects. Advantageously, the further feature recognition step allows establishing whether the wearer needs a complement of acuity, for example, if the wearer is reading, writing, using a computer, talking head to head, etc.

The invention has been described above with the aid of embodiments without limitation of the general inventive concept as defined in the claims.

The invention claimed is:

1. A method for adapting optical function of an adaptive ophthalmic lenses system, the method comprising:
    an acquisition step, during which a scene in front of a pair of adaptive ophthalmic lenses of the adaptive ophthalmic lenses system is acquired by a light sensor through a functionalized optical system, the functionalized optical system of the adaptive ophthalmic lenses system simulating an ametropia of a wearer of the ophthalmic lenses and comprising:
        the pair of adaptive ophthalmic lenses to be provided on the wearer,
        the light sensor configured to acquire the scene facing the pair of adaptive ophthalmic lenses through the functionalized optical system providing functionalized images of the scene, the scene being acquired corresponding to the light sensor acquiring light passing through the functionalized optical system and into the light sensor, and
        an eye tracking device arranged to determine gazing direction of the wearer;
    a gazing zone determining step, during which a gazing zone is determined, the gazing zone being a zone of the functionalized images of the scene acquired during the acquisition step comprising at least one gazing direction from the pair of adaptive ophthalmic lenses;
    a parameter determining step, during which the value of at least one parameter of the functionalized images of the scene acquired during the acquisition step is determined in the gazing zone of the functionalized images of the scene; and
    an adaptation step, during which an optical function of an active ophthalmic lenses system is adapted according to the value of the at least one parameter determined during the parameter determining step, wherein the at least one parameter of the functionalized images of the scene determined during the parameter determining step comprises luminosity, light transmission of the adaptive ophthalmic lenses, sharpness of the functionalized images, or any combination thereof.

2. The method according to claim 1, further comprising a calibration step, during which the eye tracking device is calibrated according to geometrical and eye-related features of the wearer.

3. The method according to claim 1, wherein the functionalized optical system is arranged so as to have at least one working distance, and during the parameter determining step, at least one parameter is related to the sharpness of the functionalized images of the scene in the gazing direction.

4. The method according to claim 3, wherein:
    the functionalized optical system is arranged so as to have at least one working distance in which the at least one working distance is two working distances,
    during the acquisition step the scene is acquired by the light sensor through the functionalized optical system using the at least two working distances,
    the method further comprises after the parameter determining step a comparison step during which values of the sharpness in the gazing zone of the functionalized images of the scene obtained through the functionalized optical system with different working distances are compared, and
    during the adaptive step the active ophthalmic lenses is adapted so as to provide clear vision to the wearer at the working distance corresponding to the at least one working distance of the functionalized optical system used to obtain the functionalized images having values of the sharpness that are greatest.

5. The method according to claim 3, further comprising after the parameter determining step a comparison step during which the sharpness of the functionalized images of the scene in the gazing direction is compared to a threshold value and during the adaptive step the active ophthalmic lenses are adapted so as to provide clear vision to the wearer at the at least one working distance when the sharpness is greater or equal to the threshold value.

6. The method according to claim 3, wherein one of the at least one working distance is smaller than or equal to 60 cm.

7. The method according to claim 3, wherein one of the at least one working distances is greater than or equal to 2 m.

8. The method according to claim 1, wherein during the parameter determining step, luminosity in the gazing direction is determined and the active ophthalmic lenses system is configured so as to adapt to the determined luminosity.

9. The method according to claim 1, wherein the parameter determining step is completed by a prior feature recognition step, during which objects in the gazing direction are analyzed in order to establish whether the wearer needs a complement of acuity.

10. A non-transitory computer readable medium comprising one or more stored sequences of instructions that are accessible to a processor and which, when executed by the processor, causes the processor to carry out the acquisition step, the parameter determining step and the adaptive step of claim 1.

11. The method according to claim 4, further comprising after the parameter determining step a comparison step during which the sharpness of the functionalized images of the scene in the gazing direction is compared to a threshold value and during the adaptive step the active ophthalmic lenses are adapted so as to provide clear vision to the wearer at the at least one working distance when the sharpness is greater or equal to the threshold value.

12. The method according to claim 4, wherein one of the at least one working distance is smaller than or equal to 60 cm.

13. The method according to claim 4, wherein one of the at least one working distance is greater than or equal to 2 m.

14. A system for adapting optical function comprising:
an adaptive ophthalmic lenses system comprising at least:
  a pair of adaptive ophthalmic lenses,
    at least one light sensor for acquiring a plurality of images of a scene in an image zone located in front of the pair of adaptive ophthalmic lenses,
    the plurality of images provided to the at least one light sensor through a functionalized optical system of the adaptive ophthalmic lenses system, the functionalized optical system of the adaptive ophthalmic lenses system simulating an ametropia of a wearer of the ophthalmic lenses, the plurality of images of the scene being acquired corresponding to the at least one light sensor acquiring light passing through the functionalized optical system and into the at least one light sensor, and
  a tracking device for determining the image zone, wherein
the adaptive ophthalmic lenses system is configured to determine at least one parameter from the plurality of images comprising: luminosity, light transmission of the adaptive ophthalmic lenses, sharpness of the images, or any combination thereof.

15. The system of claim 14, wherein the functionalized optical system includes an optical lens configured to include one or more optical corrections in accordance with optical corrections of a wearer.

16. The system of claim 14, wherein the sensor is a camera.

17. The system of claim 14, wherein the pair of adaptive ophthalmic lenses are two electro-optical lenses mounted on a spectacle frame.

18. The system of claim 14, wherein the sensor is mounted on a frame that supports the pair of adaptive ophthalmic lenses.

19. The system of claim 14, wherein the tracking device is mounted on a frame that supports the pair of adaptive ophthalmic lenses.

20. The method according to claim 1, further comprising:
a calibration step, during which the eye tracking device is calibrated according to geometrical and eye-related features of the wearer; and
after the parameter determining step a comparison step during which the sharpness of the functionalized images of the scene in the gazing direction is compared to a threshold value and during the adaptive step the active ophthalmic lenses are adapted so as to provide clear vision to the wearer at the at least one working distance when the sharpness is greater or equal to the threshold value.

* * * * *